United States Patent [19]

Topliss et

[11] 4,169,141
[45] Sep. 25, 1979

[54] 1-PEPTIDYL DERIVATIVES OF DI-O-AMINOGLYCOSYL-1,3-DIAMINOCYCLITOL ANTIBACTERIAL AGENTS

[75] Inventors: John G. Topliss; Adriano Afonso, both of West Caldwell, N.J.

[73] Assignee: Shering Corporation, Kenilworth, N.J.

[21] Appl. No.: 873,299

[22] Filed: Jan. 30, 1978

[51] Int. Cl.$^2$ .................. A61K 37/00; C07C 103/52
[52] U.S. Cl. ........................ 424/177; 260/112.5 R; 536/17 R
[58] Field of Search .................. 260/112.5 R; 536/17; 424/177

[56] References Cited

U.S. PATENT DOCUMENTS

| | | | |
|---|---|---|---|
| 4,001,208 | 1/1977 | Umezawa et al. | 536/17 |
| 4,009,264 | 2/1977 | Mizutani | 260/112.5 R |
| 4,082,735 | 4/1978 | Jones et al. | 260/112.5 R |
| 4,082,736 | 4/1978 | Jones et al. | 260/112.5 R |

Primary Examiner—Delbert R. Phillips
Attorney, Agent, or Firm—Raymond A. McDonald; Carver C. Joyner

[57] ABSTRACT

Disclosed herein are di-O-(aminoglycosyl)-1,3-diaminocyclitol antibacterial agents having on the 1-N-position of the 1,3-diaminocyclitol moiety a dipeptidyl or a tripeptidyl substituent. The compounds are useful antibacterial agents, as are their non-toxic pharmaceutically acceptable acid addition salts. Also disclosed are methods for preparing such agents from di-O-(aminoglycosyl)-1,3-diaminocyclitol antibacterial agents which are unsubstituted at the 1-N-position.

29 Claims, No Drawings

1-PEPTIDYL DERIVATIVES OF DI-O-AMINOGLYCOSYL-1,3-DIAMINOCYCLITOL ANTIBACTERIAL AGENTS

FIELD OF THE INVENTION

This invention relates to 1-N-dipeptidyl and 1-N-tripeptidyl di-O-(aminoglycosyl)-1,3-diaminocyclitol antibacterial agents. More particularly, this invention relates to di-O-(aminoglycosyl)-1,3-diaminocyclitol antibacterial agents wherein the 1-N-position bears a di or tripeptidyl substituent derived from conventional α-amino acids.

THE PRIOR ART

The antibacterial literature is replete with publications relating to the advantages of 1-N-acyl derivatives of di-O-(aminoglycosyl)-1,3-diaminocyclitol antibacterial agents. Numerous U.S. and foreign patents have issued disclosing and claiming such compounds. However, it is significant to note that the 1-N-acyl groups being disclosed and/or claimed are derived from acids having two to seven, but more frequently, up to five carbon atoms. Further, the acyl groups are most often derived from hydroxyaminocarboxylic acids. The acids employed in the prior art are almost invariably α-hydroxy-ω-amino acids. For this reason, T. H. Haskell and his co-workers investigated the antibacterial activity of synthetic analogs of butirosin and concluded inter alia that replacement of the 2-hydroxyl (α-hydroxyl) group by amino or hydrogen completely destroyed the Pseudomonas activity and markedly lowered the potency against other microorganisms. The findings were reported in Carbohydrate Research Vol. 28, 263-280 (1973).

The compounds of this invention are prepared from 4,6-di-O-(aminoglycosyl)-1,3-diaminocyclitol antibacterial agents by acylation methods known to the art. For example, the following U.S. Patents disclose methods for acylating the 1-N-position of such antibacterial agents and also disclose the structures of the respective compounds: U.S. Pat. Nos. 3,792,037, issued Feb. 12, 1974; 3,796,698, issued Mar. 12, 1974; 3,808,198, issued Apr. 30, 1974; 4,002,742, issued Jan. 11, 1977; 4,008,218 and 4,008,362, both of which issued Feb. 15, 1977. Also, of relevance is U.S. Pat. No. 4,029,882, issued June 14, 1977. The disclosures of the foregoing patents in regard to acylating procedures and structures of the various antibacterial agents, are hereby incorporated by reference.

DESCRIPTION OF THE INVENTION

This invention embraces 1-N-peptidyl derivatives of 4,6-di-O-(aminoglycosyl)-1,3-diaminocyclitol antibacterial agents including the non-toxic pharmaceutically acceptable acid addition salts thereof wherein said peptidyl moiety is derived from a di or a tripeptide having an acyl moiety selected from the group consisting of

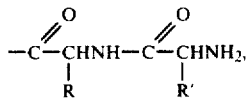

-continued

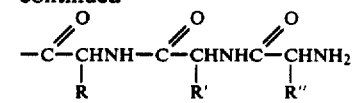

wherein R, R' and R" may be the same or different, are attached to carbon atoms which are in the L or D configuration, said R, R' and R" being members selected from the group consisting of hydrogen; $C_1$-$C_6$ alkyl including branched chain alkyl; HO—$(CH_2)_{\overline{n}}$; HO—CH—$(CH_3)$; HO—C—$(CH_3)_2$; $NH_2$—$(CH_2)_{\overline{n}}$; $NH_2$—$CH_2$—CH(OH)—$(CH_2)_{\overline{n}}$;

$NH_2$—C(=NH)—NH—$(CH_2)_{\overline{n}}$; HOOC—$(CH_2)_{\overline{n}}$;

$NH_2$—C(=O)—$(CH_2)_{\overline{n}}$; HS—$(CH_2)_{\overline{n}}$; $CH_3$S—$(CH_2)_{\overline{n}}$;

HS—C—$(CH_3)_2$

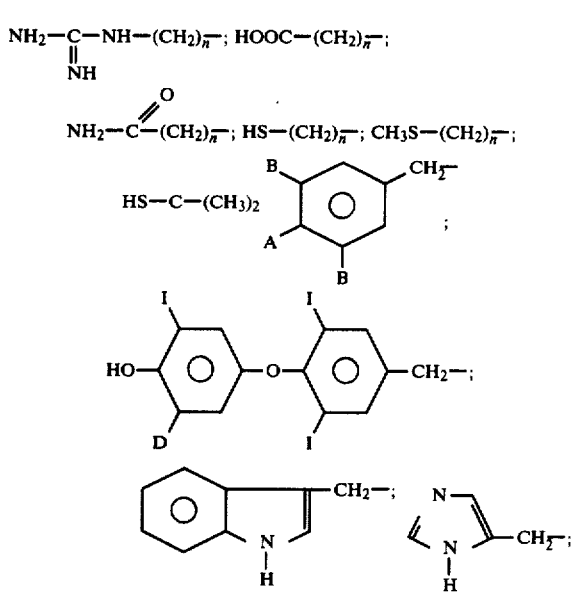

wherein A is a member of the group consisting of hydrogen and hydroxy; B is a member selected from the group consisting of hydrogen, bromo and iodo; D is a member selected from the group consisting of hydrogen and iodo; n is an integer from 1–5 and wherein R, R' and R" may be linked to the respective α-nitrogen to form a cyclic moiety selected from the group consisting of:

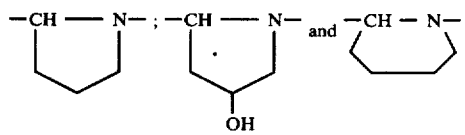

The term 4,6-di-O-(aminoglycosyl)-1,3-diaminocyclitol denotes that at least two aminoglycoside moieties are glycosidically linked to the aminocyclitol ring, one at position 4 and the other at position 6. Similarly, 1,3-diaminocyclitol are cyclic polyols having amino groups at positions 1 and 3, and optionally at other positions. Exemplary of such compounds are 2-deoxystreptamine, streptamine, 2,5-dideoxystreptamine, 1,3,5-triaminocyclohexane-4,6-diol, 2-epi-streptamine, 5-epi-2-deoxystreptamine and the like.

Exemplary of 4,6-di-O-(aminoglycosyl)-1,3-diaminocyclitol antibacterial agents are gentamicin A, gentamicin B, gentamicin $B_1$, gentamicin $C_1$, gentamicin $C_{1a}$, gentamicin $C_2$, gentamicin $C_{2a}$, gentamicin $C_{2b}$, gentamicin $X_2$, sisomicin, verdamicin, tobramycin, Antibiotic JI-20A, Antibiotic JI-20B, Antibiotic Mu-1, Antibiotic Mu-2, Antibiotic Mu-4, Antibiotic Mu-5, Antibiotic Mu-6, Antibiotic G-52, Antibiotic G-418, Antibiotic 66-40B, Antibiotic 66-40D, Kanamycin A, Kanamycin B and the like. Antibiotics Mu-1, Mu-2, Mu-4, Mu-5 and Mu-6 are known in the prior art as mutamicins 1, 2, 4, 5 and 6, respectively.

GENERAL DESCRIPTION OF THE PROCESS ASPECTS OF THE INVENTION

The 1-N-position of 4,6-di-0-(aminoglycosyl)-1,3-diaminocyclitol antibacterial agents may be acylated by a plurality of methods, most of which are set forth in the above noted prior art patents. Most of the methods generally involve protecting (blocking) reactive sites on the 4,6-di-0-(aminoglycosyl)-1,3-diaminocyclitol molecule (other than the 1-N-position), acylating the 1-N-position with a N-protected di- or tripeptide followed by deprotecting (deblocking) the resulting product. Obviously, the protecting group must be one which may be selectively removed while retaining the 1-N-acyl (1-N-peptidyl) group. Most often, the amino groups of the acylating moiety are also protected by a blocking group which is removed coincidentally with the blocking group on the 4,6-di-0-(aminoglycosyl)-1,3-diaminocyclitol. These methods are amply described in the cited prior art patents.

Also known is the order in which the various amino groups on the respective aminoglycoside antibiotics react with acylating agents. Thus, the amino groups which are more reactive than the one at the 1-position may be blocked (protected). The amino group at the 1-position of the aminocyclitol is then acylated with a N-protected dipeptidyl or tripeptidyl activated ester and the resulting intermediate deblocked thereby yielding the desired 1-N-dipeptidyl or the 1-N-tripeptidyl substituted antibiotic. For example, those 4,6-di-0-(aminoglycosyl)-1,3-diaminocyclitols having a primary amine at the C-6'-position may be reacted with trichloroethoxycarbonyl chloride, thioltrifluoroacetate or t-butoxycarbonyl azide to form the 6'-trichloroethoxycarbonyl, 6'-trifluoroacetyl or the 6'-t-butoxycarbonyl derivative, respectively.

These derivatives may subsequently be acylated at the 1-N-position with a N-protected di- or tripeptide activated ester followed by deblocking of both the C-6' and the peptidyl amino groups. When the protective group is t-butoxycarbonyl or trifluoroacetyl, the deblocking may be effected under acidic conditions. In the case of a trichloroethoxycarbonyl derivative, the deblocking is effected by reductive means.

Among the 4,6-di-0-(aminoglycosyl)-1,3-diaminocyclitol antibiotics upon which the foregoing process may be effected are the following: gentamicin B, gentamicin $C_{1a}$, sisomicin, Antibiotic JI-20A, Antibiotics Mu-1, Mu-2, Mu-4, Mu-5, Mu-6, Antibiotics 66-40B and 66-40D and the like.

Alternatively, the desired 1-N-dipeptidyl or the 1-N-tripeptidyl derivatives may be prepared by a substantially universal process directly from the respective 4,6-di-0-(aminoglycosyl)-1,3-diaminocyclitol antibiotics using the procedure described and claimed in U.S. Pat. No. 4,029,882, issued June 14, 1977, entitled SELECTIVE ACYLATION OF C-1 AMINO GROUP OF AMINOGLYCOSIDE ANTIBIOTICS.

In the patented process, a per acid addition salt of the underivatized antibiotic is treated with one equivalent of a base, preferably a strong organic base, such as triethylamine, followed by acylating with a suitably protected dipeptide or a suitably protected tripeptide activated ester thereby forming the desired 1-N-dipeptidyl or the 1-N-tripeptidyl derivative in the form of an acid addition salt. Treatment of the thus formed derivative with base or a basic ion exchange resin such as IRA-401S (Rohm and Haas, Philadelphia, Pa.) affords the desired 1-N-dipeptidyl or the 1-N-tripeptidyl derivative in the form of the free base.

A convenient method for preparing activated dipeptidyl and tripeptidyl acylating agents is to start with t-butoxycarbonyl-protected-α-amino acids which are commercially available from Cyclo Chemical Division of Travenol Laboratories, Los Angeles, Cal. 90001. These intermediates are especially convenient for preparing di and/or tripeptidyl derivatives wherein the peptidyl moiety consists of two or three different α-amino acid residues.

The following Preparations and Examples are set forth to specifically describe the best mode of carrying out the invention; however, they should not be construed to delimit same.

GENERAL PREPARATION OF REACTIVE DI AND TRIPEPTIDES

A. t-Butoxycarbonylglycine-2,4,5-Trichlorophenyl Ester

Prepare and chill a solution of 14 g. of t-butoxycarbonylglycine and 15.8 g. of 2,4,5-trichlorophenol in 200 ml. of ethyl acetate. Add with stirring 18.2 g. of dicyclohexylcarbodiimide in small portions. Stir the reaction mixture at room temperature for 16 hours, filter and evaporate the filtrate to a residue. Wash the residue by triturating with hexane, then crystallize from ethyl ether to obtain thereby the title product (m.p. 100°–103° C.).

B. t-Butoxycarbonyl-glycyl-glycine-methyl Ester

Prepare a solution of 1.98 g. of glycine methyl ester hydrochloride in dimethylformamide containing 8 ml. of methanol and 1.42 g. of triethylamine. Cool and stir the solution while adding 5.0 g. of t-butoxycarbonylglycine-2,4,5-trichlorophenyl ester in 25 ml. of dimethylformamide. Stir the reaction mixture overnight, filter and evaporate the filtrate to dryness under reduced pressure. Chromatograph the residue on 150 g. of silica gel and collect the desired product which is eluted by an ethyl acetate:chloroform (1:9) mixture. Evaporate the eluate to dryness and crystallize from hexane to obtain the title product (m.p. 132°–135° C.).

C. t-Butoxycarbonyl-glycyl-glycine

Add, to a solution of t-butoxycarbonyl-glycyl-glycine methyl ester (3.9 g.) in tetrahydrofuran (30 ml.) and water (30 ml.), 16 ml. of 1 N sodium hydroxide dropwise. Stir the mixture until homogenous (1 ½ hours), then acidify to pH 3 with dilute hydrochloric acid and evaporate to dryness. Suspend the residue in acetone, filter and evaporate the filtrate to dryness to afford the title product (m.p. 125°–128° C.).

D. t-Butoxycarbonyl-glycyl-glycine-2,4,5-Trichlorophenyl Ester

Dissolve 2.5 g. of t-butoxycarbonyl-glycyl-glycine in dimethylformamide (20 ml.) containing 2,4,5-trichlorophenol (2.13 g.) and N-hydroxysuccinimide (1.4 g.). Cool the solution in an ice bath and stir while adding dicyclohexylcarbodiimide (2.44 g.) in dimethylformamide (5 ml.). Allow the reaction mixture to stand at room temperature for 48 hours, filter the reaction mixture and evaporate the filtrate to dryness under reduced pressure. Chromatograh the residue on silica gel (150 g.). The desired product is eluted with 20% ethyl acetate/chloroform and crystallized from ether-hexane (m.p. 90°-91° C.).

In a similar manner, by substituting an equivalent quantity of t-butoxycarbonyl derivatives and the methyl esters of other α-amino acids and following the process set forth above, the respective N-protected activated dipeptide derivatives may be prepared. Exemplary of such α-amino acids are the following: serine, alanine, lysine, cysteine, glutamic acid, histidine, leucine, isoleucine, methionine, phenylalanine, proline, threonine, tyrosine, valine, asparagine, aspartic acid, tryptophan and the like.

E. t-Butoxycarbonyl-glycyl-glycyl-glycine-methyl Ester

Dissolve 2.8 g. of t-butoxycarbonyl-glycyl-glycine methyl ester in 1 N hydrochloric acid in acetic acid (56 ml.) and allow the solution to stand for 20 minutes. Evaporate the solution to dryness. Dissolve the residue in dimethylformamide (35 ml.), cool in an ice bath and add triethylamine (1.15 g.) followed by t-butoxycarbonyl-glycine, 2,4,5-trichlorophenyl ester (4.1 g.) with stirring. Stir the reaction mixture for 24 hours and then evaporate under reduced pressure. Triturate residue with ethyl acetate and collect the insoluble product by filtration (m.p. 122°-128° C.).

F. t-Butoxycarbonyl-glycyl-glycyl-glycine

Add to a solution of t-butoxycarbonyl-glycyl-glycyl-glycine methyl ester (4.1 g.) in tetrahydrofuran (30 ml.) and water (30 ml.) dropwise with stirring 1 N sodium hydroxide (13.6 ml.). Stir the reaction mixture for 16 hours, acidify to pH 3 with dilute hydrochloric acid and then evaporate to dryness under reduced pressure. Suspend the residue in acetone, filter and evaporate the filtrate to dryness to afford the title product (m.p. 115°-120° C.).

G. -Butoxycarbonyl-glycyl-glycyl-glycine-2,4,-Trichloropehnyl Ester

Cool a solution of t-butoxycarbonyl-glycyl-glycyl-glycine (500 mg.) and 2,4,5-trichlorophenol (340 mg.) in chloroform (10 ml.) in an ice bath. Add dicyclohexylcarbodiimide (390 mg.) in chloroform (2 ml.) dropwise. Allow the mixture to stand at 4° C. for 16 hours, filter and evaporate the filtrate to dryness. Chromatograh the residue on silica gel (40 g.). Elution with 30% acetone/chloroform affords the title product which may be crystallized from ether (m.p. 128°-130° C.).

In a similar manner, by substituting an equivalent quantity of t-butoxycarbonyl derivatives and the methyl esters of other α-amino acids and following the process set forth above, the respective N-protected activated tripeptide derivatives may be prepared, Exemplary of such α-amino acids are the following: serine, alanine, lysine, cysteine, glutamic acid, histidine, leucine, isoleucine, methionine, phenylalanine, proline, threonine, tyrosine, valine, asparagine, aspartic acid, tryptophan and the like.

PREPARATION OF PROTECTED AMINOGLYCOSIDES

1. 6'-N-Trifluoroacetylsisomicin

Dissolve 20 g. of sisomicin in 1.2 liters of anhydrous methanol and add dropwise a solution of 6 ml. of ethyl thioltrifluoroacetate in 60 ml. of methanol over a 3 hour period with stirring. Allow the reaction to proceed for 18 hours at room temperature and remove the solvent in vacuo to give a residue of 23.8 g. of product of approximately 95% purity having the following physicochemical properties:

Mass Spectral Data: m/e 543 M$^+$, other definitive peaks at m/e 413, 395, 385, 362, 223 and 126. NMR (60MHz, D$_2$O) δ5.37 doublet, J=2Hz, H-1'; 5.12 doublet, J=4Hz, H-1"; 4.96 broad singlet, H-4'; 2.57, singlet, N-CH$_3$; 1.26 singlet, C-CH$_3$.

In a manner similar to that described in Preparation A treat an equivalent quantity of each of the following antibiotics with ethylthioltrifluoroacetate in methanol:
a. gentamicin C$_{1a}$,
b. gentamicin B,
c. Antibiotic JI-20A,
d. Antibiotic 66-40B,
e. Antibiotic 66-40D,
f. the 5-epi, 5-epiamino-5-deoxy and the 5-epi-azido-5-deoxy analogs of the foregoing,
g. Antibiotic Mu-1,
h. Antibiotic Mu-2,
i. Antibiotic Mu-4,
j. Antibiotic Mu-5,
k. tobramycin Isolate the resultant products in a manner similar to that described in Preparation A to obtain, respectively,
a. 6'-N-trifluoroacetyl-gentamicin C$_{1a}$,
b. 6'-N-trifluoroacetyl-gentamicin B,
c. 6'-N-trifluoroacetyl-Antibiotic JI-20A,
d. 6'-N-trifluoroacetyl-Antibiotic 66-40B,
e. 6'-N-trifluoroacetyl-Antibiotic 66-40D,
f. the 5-epi, 5-epi-amino-5-deoxy, and the 5-epi-azido-5-deoxy analogs of the foregoing,
g. 6'-N-trifluoroacetyl-Antibiotic Mu-1,
h. 6'-N-trifluoroacetyl-Antibiotic Mu-2,
i. 6'-N-trifluoroacetyl-Antibiotic Mu-4,
j. 6'-N-trifluoroacetyl-Antibiotic Mu-5,
k. 6'-N-trifluoroacetyl-tobramycin

2. 6'-N-t-Butoxycarbonylgentamicin C$_{1a}$

Dissolve 2.69 g. of gentamicin C$_{1a}$ in 60 ml. of methanol:water (1:1), cool to 5° C. and add 1.815 ml. of triethylamine. Add with stirring 1.91 g. of t-butoxycarbonyl azide dropwise. Stir the mixture at 5° C. for 18 hours. Add 20 ml. of Amberlite IRA-401S resin (OH$^\ominus$) form, stir for 30 minutes, filter and evaporate the filtrate to dryness in vacuo. Chromatogragh the crude product over silica gel (350 g.) using the lower phase of a 2:1:1 chloroform:methanol:concentrated ammonium hydroxide solvent system as eluant. Take 3 ml. fractions and monitor their contents by TLC. Combine fractions containing the major reaction product and evaporate to obtain the title compound of this example (0.42 g., 13%) [α]$_D^{26}$+137° (MeOH), PMR δ 1.23 (3H, s, 1C-CH$_3$), 1.45 (9H, s, C-(CH$_3$)$_3$), 2.53 (3H, s, N-CH$_3$) δ 5.08 (2H, overlapping doublets, J=3.5Hz, H-1' and H-1") PPM. Mass Spectrum m/e 550 [(M+1)$^+$] and m/e 549 (M$^+$).

3. 6'-N-t-Butoxycarbonylgentamicin B

Dissolve 1 g. of gentamicin B in 30 ml. of 50% aqueous methanol and cool to 5° C. Add 0.297 g. of t-butoxycarbonyl azide dropwise with stirring followed by 0.186 ml. of triethylamine and stir the resulting solution for 18 hours. Evaporate the reaction mixture in vacuo to a residue and chromatograph the residue on 100 g. of silica gel using the lower phase of a 2:1:1 chloroform methanol:concentrated ammonium hydroxide solvent system as eluant. Collect 2 ml. fractions and monitor the column effluent by TLC. Combine fractions containing like material (fractions 180–230) and evaporate to botain 0.830 g. 6'-N-t-butoxycarbonylgentamicin B having the following physical constants: PMR (60 MHz, $D_2O$) $\delta 1.21$ (3H, s, C-$CH_3$), 1.42 (9H, s, C($CH_3$)$_3$), 2.53 (3H, s, N-$CH_3$), 5.2 (1H, d, J = 4.5Hz, H-1″), 5.23 (1H, d, J = 3.0 Hz, H-1′) PPM.

In the manner similar to that described in Preparation 2 or 3, treat an equivalent quantity of the antibiotics enumerated after Preparation 1 to obtain thereby the following:

6'-N-t-butoxycarbonyl-Antibiotic JI-20A,
6'-N-t-butoxycarbonyl-Antiobiotic 66-40B,
6'-N-t-buoxycarbonyl-Antibiotic 66-N-t-butoxycarbonyl-Antibiotic 40D,
the 5-epi, 5-epi-amino-5-deoxy and the 5-epi-azido-5-deoxy analogs of the foregoing, 6'-N-t-butoxycarbonyl-Antibiotic Mu-1,
6'-N-t-butoxycarbonyl-Antibiotic Mu-2,
6'-N-t-butoxycarbonyl-Antibiotic Mu-4,
6'-N-t-butoxycarbonyl-Antibiotic Mu-5, and
6'-N-t-butoxycarbonyl-tobramycin The compounds of this invention may be employed in the form of 1-N-dipeptidyl or 1-N-tripeptidyl free amines or in the form of non-toxic pharmaceutically acceptable acid addition salts. The preparation of the free amines and of the non-toxic pharmaceutically acceptable acid addition salts thereof are set forth in the following examples.

The Preparations described above and the Examples set forth below should not be construed as limiting the scope of this invention.

EXAMPLE 1

1-N-DIGLYCYL-SISOMICIN

A.
6'-t-Butoxycarbonyl-1-N-(t-butoxy-glycyl-glycyl)-sisomicin

Dissolve 2 g. of 6'-t-butoxycarbonylsisomicin (prepared by the procedure described in Preparation 2) in 20 ml. of dimethylformamide and chill. Add dropwise with stirring, a solution of 1 g. of t-butoxycarbonyl-glycyl-glycine-2,4,5-trichlorophenyl ester in 10 ml. of dimethylformamide. Stir the reaction mixture at room temperature for 16 hours. Evaporate the solution under reduced pressure to a residue. Chromatograph the residue on 170 g. of silica gel eluting with the solvent system consisting of chloroform:methanol:7% ammonium hydroxide (2:1:1 v/v). Monitor the column by thin layer chromatography on silica gel plates using the solvent system consisting of chloroform:methanol:concentrated ammonium hydroxide:water (60:30:3:2) as the developing solvent. Combine fractions containing the major product and evaporate to dryness and obtain thereby the title product of this step (m.p. 134°–142° C., $[\alpha]_D^{26} + 124.5°$ ($H_2O$)).

B. 1-N-(Diglycyl)Sisomicin

Dissolve 0.52 g. of the product of Step A. in 5 ml. of trifluoroacetic acid and, after about one minute, dilute the solution with 50 ml. of ethyl ether. Filter the resulting suspension and dissolve the precipitate in 10 ml. of water. Pass the aqueous solution through a column containing 20 ml. of Amberlite ® IRA-401S ion exchange resin. Collect the eluate and lyophilize to obtain thereby 1-N-(diglycyl)-sisomicin, m.p. 120°–130° C.; $[\alpha]_D^{26} + 138°$ ($H_2O$).

EXAMPLE 2

1-N-(Diglycyl) Gentamicin B

A. Prepare 6'-N-t-Butoxycarbonyl Gentamicin B as shown in Preparation 3.

B.
1-N-(t-butoxycarbonylglycyl)-6'-N-t-butoxycarbonyl gentamicin B

To a cold solution of 2.0 g. of 6'-N-t-butoxycarbonyl gentamicin B in dimethylformamide (20 ml.) was added dropwise with stirring a solution of t-butoxycarbonyl-glycyl-glycine-2,4,5-trichlorophenylester (1 g.) in dimethylformamide (10 ml.). The reaction mixture was stirred at room temperature for 16 hours and then evaporated under reduced pressure. The residue was chromatographed on silica gel (170 g.) and eluted with the solvent system consisting of chloroform:methanol:7% ammonium hydroxide (2:1:1). The progress of the column was followed by TLC on silica gel plates ($CHCl_3$:MeOH:$NH_4OH$:$H_2O$ -60:30:3:2 as developing solvent). The fractions homogenous in the major product were combined and evaporated to dryness to afford the title product, m.p. 186°–190° C.; $[\alpha]_D^{26} = +80°$ C. (dimethylformamide).

C. 1-(glycylglycyl) Gentamicin B

The above product (0.52 g.) was dissolved in trifluoroacetic acid (5 ml.) and after 60 seconds was diluted with ether in water and passed through a column of Amberlite 401-S ion exchange resin (20 ml.). The water eluate was lyophilized to afford the desired product, m.p. 156°–162° C.; $[\alpha]_D^{26} = +117°$ C. ($H_2O$).

In a similar manner, perform the process of Examples 1 and 2 on an equivalent quantity of the 6'-N-t-butoxycarbonyl derivatives of the following antibacterial agents: Antibiotic 66-40B, Antibiotic 66-40D, the 5-epi, 5-epiamino-5-deoxy and the 5-epiazido-5-deoxy analogs of the foregoing, Antibiotic Mu-1, Antibiotic Mu-2, Antibiotic Mu-4, Antibiotic Mu-5, Antibiotic Mu-6, tobramycin, gentamicin $C_{1a}$, kanamycin A and kanamycin B.

Isolate the resultant products to obtain thereby: 1-N-(diglycyl) Antibiotic 66-40B, 1-N-(diglycyl) Antibiotic 66-40D, the 5-epi, 5-epiamino-5-deoxy, and the 5-epiazido-5-deoxy analogs of the foregoing, 1-N-(diglycyl) Antibitic Mu-1, 1-N-(diglycyl) Antibiotic Mu-2, 1-N-(diglycyl) Antibiotic Mu-4, 1-N-(diglycyl) Antibiotic Mu-5, 1-N-(diglycyl) Mu-6, 1-N-(diglycyl) tobramycin, 1-N-(diglycyl) gentamicin $C_{1a}$, 1-N-(diglycyl) kanamycin A and 1-N-(diglycyl) kanamycin B.

EXAMPLE 3

1-N-(Diseryl) Verdamicin

A. 1-N-(t-Butoxycarbonylserylseryl) Verdamicin

Dissolve with stirring 1.25 g. of verdamicin sulfate in a mixture of 6.7 ml. of dimethylformamide and 13.3 ml. of water. Add 0.18 g. of triethylamine and after 10 minutes, add 0.85 g. of t-butoxycarbonylserylserine-2,4,5-trichlorophenyl ester (prepared by the process of Preparations B-D above) in 2.0 ml. of dimethylformamide. Stir the reaction mixture for 16 hours. Evaporate the solution under reduced pressure to a residue. Purify the crude reaction product by chromatography as described in Example 1 step B to obtain thereby 1-N-(t-butoxycarbonylserylseryl) verdamicin.

B. 1-N-(Diseryl) Verdamicin

Dissolve the product from step A in 5.0 ml. trifluoroacetic acid and allow to stand for about one minute. Dilute the solution with 50 ml. of ether, filter the resulting precipitate and dissolve it in about 25 ml. of water and treat with 20 ml. of Amberlite 401-S ion exchange resin (OH̄ form). Lyophilize the aqueous solution and obtain thereby the product of this example, 1-N-(diseryl) verdamicin.

In a similar manner, perform the process of Example 3 on an equivalent quantity of a per acid addition salt of the following antibiotics: gentamicin A, gentamicin B, gentamicin B$_1$, gentamicin C$_1$, gentamicin c$_{1a}$, gentamicin C$_2$, gentamicin C$_{2a}$, gentamicin C$_{2b}$, gentamicin X$_2$, sisomicin, tobramycin, Antibiotic JI-20A, Antibiotic JI-20B, Antibiotic Mu-1, Antibiotic Mu-2, Antibiotic Mu-4, Antibiotic Mu-5, Antibiotic Mu-6, Antibiotic G-52, Antibiotic G-418, Antibiotic 66-40B, Antibiotic 66-40D, kanamycin A and kanamycin B.

Isolate the resultant products to obtain thereby 1-N-(diseryl) gentamicin A, 1-N-(diseryl) gentamicin B, 1-N-(diseryl) gentamicin B$_1$, 1-N-(diseryl) gentamicin C$_1$, 1-N-(diseryl) gentamicin C$_{1a}$, 1-N-(diseryl) gentamicin C$_2$, 1-N-(diseryl) gentamicin C$_{2a}$, 1-N-(diseryl) gentamicin C$_{2b}$, 1-N-(diseryl) gentamicin X$_2$, 1-N-(diseryl) sisomicin, 1-N-(diseryl) tobramycin, 1-N-(diseryl) Antibiotic JI-20A, 1-N-(diseryl) Antibiotic JI-20B, 1-N-(diseryl) Antibiotic Mu-1, 1-N-(diseryl) Antibiotic Mu-2, 1-N-(diseryl) Antibiotic Mu-4, 1-N-(diseryl) Antibiotic Mu-5, 1-N-(diseryl) Antibiotic Mu-6, 1-N-(diseryl) Antibiotic G-52 1-N-(diseryl) Antibiotic G-418, 1-N-(diseryl) Antibiotic 66-40B, 1-N-(diseryl) Antibiotic 66-40D, 1-N-(diseryl) kanamycin A and 1-N-(diseryl) kanamycin B.

EXAMPLE 4

A. 1-N-(t-Butoxycarbonyl-glycyl-glycyl-glycyl) Sisomicin

Dissolve with stirring 5 g. sisomicin sulfate in a mixture of 50 ml. dimethylformamide and 50 ml. water. Add 0.72 g. of triethylamine and stir for 10 minutes. Add 3.5 g. of t-butoxycarbonyl-glycyl-glycine-2,4,5-trichlorophenyl ester (see Preparation G above) in 10 ml. dimethylformamide and stir the reaction mixture for 16 hours at room temperature. Evaporate the solution to a residue under reduced pressure and treat the residue as described in Example 3 step A to obtain the title compound, m.p. 126°-129° C.; $[\alpha]_D^{26} + 86°$ C. (H$_2$O).

B. 1-N-(Triglycyl) Sisomicin

Dissolve the product from step A in 15 ml. of trifluoroacetic acid and repeat the process described in Example 3 step B to obtain thereby the product of this example 1-N-(triglycyl) sisomicin, m.p. 152°-155° C.; $[\alpha]_D^{26} + 121°$ C.(H$_2$O).

In a similar manner, perform the process of Example 4 on an equivalent quantity of a per acid addition salt of the following antibiotics: gentamicin A, gentamicin B, gentamicin B$_1$, gentamicin C$_1$, gentamicin C$_{1a}$, gentamicin C$_2$, gentamicin C$_{2b}$, gentamicin X$_2$, verdamicin, tobramycin, Antibiotic JI-20A, Antibiotic JI-20B, Antibiotic Mu-1, Antibiotic Mu-2, Antibiotic Mu-4, Antibiotic Mu-5, Antibiotic Mu-6, Antibiotic G-418, Antibiotic 66-40B, Antibiotic 66-40D, kanamycin A and Kanamycin B.

Isolate the resultant products to obtain thereby: 1-N-(triglycyl) gentamicin A, 1-N-(triglycyl) gentamicin B, 1-N-(triglycyl) gentamicin B$_1$, 1-N-(triglycyl) gentamicin C$_1$, 1-N-(triglycyl) gentamicin C$_{1a}$, 1-N-(triglycyl) gentamicin C$_2$, 1-N-(triglycyl) gentamicin C$_{2a}$, 1-N-(triglycyl) gentamicin C$_{2b}$, 1-N-(triglycyl) gentamicin X$_2$, 1-N-(triglycyl) sisomicin, 1-N-(triglycyl) tobramycin, 1-N-(triglycyl) Antibiotic JI-20A, 1-N-(triglycyl) Antibiotic JI-20B, 1-N-(triglycyl) Antibiotic Mu-1, 1-N-(triglycyl) Antibiotic Mu-2, 1-N-(triglycyl) Antibiotic Mu-4, 1-N-(triglycyl) Antibiotic Mu-5, 1-N-(triglycyl) Antibiotic Mu-6, 1-N-(triglycyl) Antibiotic G-52, 1-N-(triglycyl) Antibiotic G-418, 1-N-(triglycyl) Antibiotic 66-40B, 1-N-(triglycyl) Antibiotic 66-40D, 1-N-(triglycyl) kanamycin A and 1-N-(triglycyl) kanamycin B.

In like manner by substituting an equivalent quantity of a suitably protected activated ester of other tripeptides for t-butoxycarbonyl-glycyl-glycyl-glycine-2,4,5-trichlorophenyl ester and by repeating the processes of Examples 1-4, other than 1-N-tripeptidyl derivatives of the above named antibiotics may be prepared. Exemplary of such tripeptides are those derived from such α-amino-acids as alanine, valine, leucine, tyrosine, methionine, serine, threonine, proline, lysine, crysteine, histidine, isoleucine, asparagine, aspartic acid, glutamic acid, tryptophan and the like. Included also are dipeptides derived from two α-amino acids. In either case the peptidyl derivatives may be of the mixed variety which are derived from two or three different α-amino acids. Exemplary of such mixed peptidyl derivatives are those set forth in the following table:

Table 1

| Compound | MP° C. | $[\alpha]_D^{26}$(H$_2$O) |
|---|---|---|
| 1-N-(L-leucyl-glycol)sisomicin | 115°–119° | + 135° |
| 1-N-(glycyl-L-leucyl) sisomicin | 132°–136° | + 98° |
| 1-N-(glycyl-L-seryl) sisomicin | 148°–151° | + 100° |
| 1-N-(L-seryl-glycyl) sisomicin | 136°–140° | +127° |
| 1-N-(glycyl-L-α-α-diaminobutyryl) sisomicin | 142°–146° | + 107° |
| 1-N-(L-α,α-diaminobutyryl-glycyl) sisomicin | 136°–140° | + 122° |

EXAMPLE 6

Acid Addition Salts

A. Sulfate Salts

Dissolve 5.0 g. of 1-N-diseryl sisomicin in 25 ml. of water and adjust the pH of the solution to 4.5 with 1N sulfuric acid. Precipitate into about 300 ml. of methanol with vigorous agitation. Continue the agitation for about 10–20 minutes and filter. Wash the precipitate with methanol and dry at about 60° C. in vacuo to obtain 1-N-diserylsisomicin sulfate.

B. Hydrochloride Salts

Dissolve 5.0 g of 1-N-diglycyl sisomicin in 25 ml. of water. Acidify with 2N hydrochloric acid to pH 5.0 and lyophilize to obtain 1-N-diglycyl sisomicin hydrochloride.

The foregoing procedures are of general utility for preparing non-toxic pharmaceutically acceptable acid addition salts of inorganic acids and of organic acid such as acetic, propionic, cyclopropyl carboxylic, maleic, stearic, fuoric, nicotinic, picolinic acids and the like. Preferred non-toxic pharmaceutically acceptable acid addition salts are those derived from mineral acids.

In Vitro Antibacterial Activity

As previously stated, the compounds of this invention are antibacterial agents having a broad spectrum of activity. The compounds exhibit good activity against sisomicin sensitive strains of Enterobacter, *Escherichia coli*, Proteus, Klebsiella, Providencia, Serratia and Pseudomonas. Additionally, the compounds are active against Pseudomonas strains capable of producing enzymes which can phosphorylate neomycin and kanamycin. The compounds are also active against sisomicin resistant strains of *E. coli* and Klebsiella which are known to be capable of producing gentamicin adenyltransferase [GAS or ANT (2")]. The compounds have a definite but limited inhibitory activity against sisomicin resistant strains of *E. coli* and Pseudomonas which are known to be capable of producing 3-N-gentamicin acetyltransferase [GAT or AAC (3) and GAT III or AAC (3) II]. Thus, the compounds of this invention may be used in conjunction with soaps and detergents to clean and disinfect the surfaces of laboratory equipment such as tables, scales, cages and the like.

In Vivo Antibacterial Activity

A. The compounds of this invention exhibit an unexpectedly high intravenous $LD_{50}$ when administered to male CF1(Carworth Farms) mice, the $LD_{50}$ being about 185 mg/kg which is about two to four times that observed with gentamicin or sisomicin.

B. Mouse protection tests were performed in the usual manner using CF1 (Carworth Farms) mice weighing 18 to 20 g. each. The $PD_{50}$ values are in substantial agreement with those expected in view of the in vitro results, i.e. the compounds, like sisomicin exhibit slight protection against Pseudomonas infections caused by known producers of GAT I. On the other hand, the compounds of the instant invention exhibit good protective activity against the Klebsiella infections caused by Klebsiella known to be producers of GAS. Thus, the compounds of this invention may be used to control or eradicate susceptible bacterial strains in warm blooded animals, particularly in laboratory animals.

In general, the dosage of 1-N-dipeptidyl or tripeptidyl derivatives of the 4,6-di-0-(aminoglycosyl)-1,3-diaminocyclitol antibacterial agent administered is dependent upon such factors as the age and weight, mode of administration, the severity of the bacterial infection, the animal species being treated and, where known, the infecting organism. However, for all but the most refractory infections a dosage of 7.5 to 15 mg/kg per day in divided doses is administered.

As is true of the parent antibiotics from which the instant compounds are prepared, certain compounds or groups thereof within a genus are preferred over others for various reasons including increased potency, lower toxicity, broader spectra or the like. A preferred group of compounds of this invention are those 1-N-dipeptidyl and 1-N-tripeptidyl derivatives of 4,6-di-0-(aminoglycosyl)-1,3-diaminocyclitols wherein the glycosyl group attached to the 6 position of the diaminocyclitol moiety is derived from garosamine. A particularly preferred group of compounds of this invention are those 1-N-dipeptidyl and 1-N-tripeptidyl derivatives of 4,6-di-0-(aminoglycosyl)-1,3-diaminocyclitol antibiotics wherein said 4-0-aminoglycosyl moiety has a double bond bridging positions 4' and 5' thereof and said 6-0-aminoglycosyl moiety is derived from garosamine. This group embraces the 1-N-dipeptidyl and 1-N-tripeptidyl derivatives of sisomicin, verdamicin, Antibiotic G-52, Antibiotic Mu-1, Antibiotic Mu-2, Antibiotic Mu-4, Antibiotic Mu-5 and Antibiotic Mu-6. A most preferred group of compounds of this invention are the 1-N-dipeptidyl derivatives of sisomicin, a preferred species of which is 1-N-diglycylsisomicin.

In order to elicit an antibacterial response in warm blooded animals having a susceptible bacterial infection, the compounds of this invention are usually employed in the form of pharmaceutical dosage forms containing the active compounds and compatible carriers. Exemplary of such dosage forms are the following:

| Ingredients | Formulation 1 Tablets | | |
|---|---|---|---|
| | 10 mg. Tablet | 25 mg. Tablet | 100 mg. Tablet |
| 1-N-diglycylsisomicin | 10.50* mg. | 26.25* mg. | 105.00 mg. |
| Lactose, impalpable Powder | 197.50 mg. | 171.25 mg. | 126.00 mg. |
| Corn Starch | 25.00 mg. | 25.00 mg. | 35.00 mg. |
| Polyvinylpyrrolidone | 7.50 mg. | 7.50 mg. | 7.50 mg. |
| Magnesium Stearate | 2.50 mg. | 2.50 mg. | 3.50 mg. |

*In formulations 1 and 3 the * indicates that a 5% manufacturing overcharge is used

Procedure

Prepare a slurry consisting of the 1-N-diglycylsisomicin, lactose and polyvinylpyrrolidone. Spray dry the slurry. Add the corn starch and the magnesium stearate. Mix and compress into tablets.

| Ingredients | Formulation 2 Ointment |
|---|---|
| 1-N-diglycyl-gentamicin B | 1.0 g. |
| Methyl Paraben U.S.P. | 0.5 g. |
| Propyl Paraben U.S.P. | 0.1 g. |
| Petrolatum | to 1000 g. |

Procedure

Melt the petrolatum. Mix the 1-N-diglycyl gentamicin B, methyl paraben and propyl paraben with about 10% of the molten petrolatum. Pass the mixture through a colloid mill. Add the remainder of the petrolatum with agitation and cool the mixture until it becomes semi-solid then pass into suitable containers.

| Formulation 3 Injectable Solution | | |
|---|---|---|
| Ingredients | Per 2.0 ml vial | Per 50 liters |
| 1-N-triglycylsisomicin sulfate | 84.0* mg. | 2100.0 g. * |
| Methyl Paraben U.S.P. | 3.6 mg. | 90.0 g. |
| Propyl Paraben U.S.P. | 0.4 mg. | 10.0 g. |
| Sodium Bisulfite U.S.P. | 6.4 mg. | 160.0 g. |
| Disodium Ethylenediamine Tetraacetate dihydrate, R.G. | 0.2 mg. | 5.0 g. |
| Water U.S.P. q.s. | 2.0 mg. | 50.0 liters |

* In formulations 1 and 3 the * indicates a 5% manufacturing overcharge is used

Procedure for a 50.0 Liter Batch

Charge approximately 35 liters of water for injection to a suitable stainless steel jacketed vessel and heat to about 70° C. Charge the methyl paraben and the propyl paraben to the heated water for injection and dissolve the agitation. When the parabens are completely dissolved, cool the contents of the tank to 25°-30° C. by circulating cold water through the tank jacket. Sparge the solution with nitrogen gas for at least 10 minutes and keep covered with nitrogen during subsequent processing. Charge and dissolve the disodium EDTA and the sodium bisulfite. Charge and dissolve the 1-N-triglycylsisomicin sulfate. Adjust the batch volume to 50.0 liters with water and agitate until homogenous. Under sterile conditions, filter the solution through a suitable bacteria retentive filter collecting the filtrate in a sterile filling tank. Transfer the filtrate aseptically in to sterile pyrogen-free multiple dose vials, stopper and seal.

What is claimed is:

1. 1-N-peptidyl derivatives of 4,6-di-O-(aminoglycosyl)-1,3-diaminocyclitol antibacterial agents including the non-toxic pharmaceutically acceptable acid addition salts thereof wherein said peptidyl moiety is derived from a di or tripeptide having an acyl moiety selected from the group consisting of

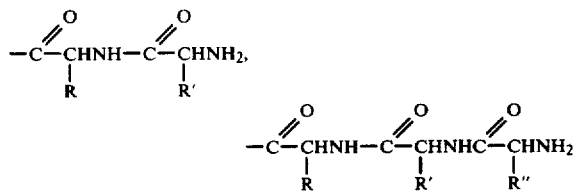

wherein R, R' and R" may be the same or different, are attached to carbon atoms which are in the L or D configuration, said R, R' and R" being members selected from the group consisting of hydrogen; $C_1$-$C_6$ $C_1$-$C_6$ alkyl including branched chain alkyl; HO—$(CH_2)_{\overline{n}}$; HO—CH—$(CH_3)$; HO—$(CH_3)_2$; $NH_2$—$(CH_2)_{\overline{n}}$; $NH_2$—$CH_2$—CH(OH)—$(CH_2)_{\overline{n}}$;

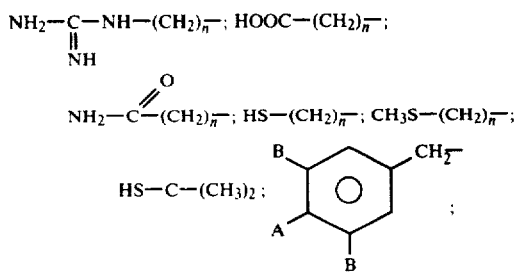

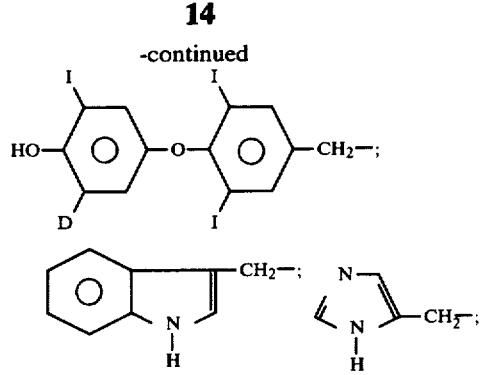

wherein A is a member of the group consisting of hydrogen and hydroxy; B is a member selected from the group consisting of hydrogen, bromo and iodo; D is a member selected from the group consisting of hydrogen and iodo; n is an integer from 1–5 and wherein R, R' and R" may be linked to the respective α-nitrogen to form a cyclic moiety selected from the group consisting of:

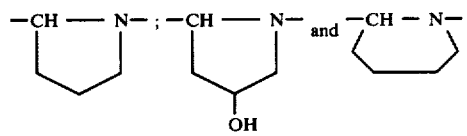

2. A compund of claim 1 wherein the acyl moiety has the formula

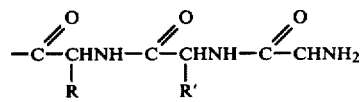

group wherein R and R' are as defined in said claim 1.

3. A compound of claim 1 wherein the acyl moiety has the formula

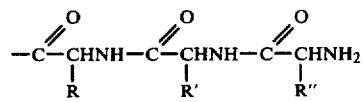

group wherein R, R' and R" are as defined in said claim 1.

4. A 1-N-peptidyl derivative of a 4,6-di-O-(aminoglycosyl)-1,3-diaminocyclitol antibacterial agent of claim 2 selected from the group consisting of gentamicin A, gentamicin B, gentamicin $B_1$, gentamicin $C_1$, gentamicin $C_{1a}$, gentamicin $C_2$, gentamicin $C_{2a}$, gentamicin $C_{2b}$, gentamicin $X_2$, sisomicin, verdamicin, tobramycin, Antibiotic JI-20A, antibiotic JI-20B, Antibiotic Mu-1, Antibiotic Mu-2, Antibiotic Mu-4, Antibiotic Mu-5, Antibiotic Mu-6, Antibiotic G-52, Antibiotic G-418, Antibiotic 66–40B, Antibiotic 66–40D, kanamycin A and kanamycin B.

5. A 1-N-peptidyl derivative of a 4,6-di-O-(aminoglycosyl)-1,3-diaminocyclitol antibacterial agent of claim 3 selected from the group consisting of gentamicin A, gentamicin B, gentamicin $B_1$, gentamicin $C_1$, gentamicin $C_{1a}$, gentamicin $C_2$, gentamicin $C_{2a}$, gentamicin $C_{2b}$, gentamicin $X_2$, sisomicin, verdamicin, tobramycin, Antibiotic JI-20A, Antibiotic JI-20B, Antibiotic Mu-1, Antibiotic Mu-2, Antibiotic Mu-4, Antibiotic Mu-5, Antibiotic Mu-6, Antibiotic G-52, Antibiotic G-418, Antibiotic 66-40B, Antibiotic 66-40D, kanamycin A and kanamycin B.

6. A 1-N-peptidyl derivative of a 4,6-di-0-(aminoglycosyl)-1,3-diaminocyclitol antibacterial agent of claim 2 wherein said 4-0-(aminoglycosyl) moiety has a double bond briding the 4',5'-position of a compund selected from the group consisting of sisomicin, verdamicin, Antibiotic G-52, Antibiotic 66-40B, Antibiotic 66-40D, Antibiotic Mu-1,Antibiotic Mu-2, Antibiotic Mu-4, Antibiotic Mu-5 and Antibiotic Mu-6.

7. A 1-N-peptidyl derivative of a 4,6-di-0-(aminoglycosyl)-1,3-diaminocyclitol antibacterial agent of claim 3 wherein said 4-0-(aminoglycosyl) moiety has a double bond bridging the 4',5'-position of a compound selected from the group consisting of sisomicin, verdamicin, Antibiotic G-52, Antibiotic 66-40B, Antibiotic 66-40D, Antibiotic Mu-1, Antibiotic Mu-2, Antibiotic Mu-4, Antibiotic Mu-5 and Antibiotic Mu-6.

8. A compound of claim 6, said compound being a 1-N-dipeptidyl derivative of sisomicin selected from the group consisting of 1-N-(diglycyl)-sisomicin, 1-N-(L-leucyl-glycyl) sisomicin, 1-N-(glycyl-L-leucyl) sisomicin, 1-N-glycyl-L-seryl) sisomicin, 1-N-(L-seryl-glycyl)sisomicin, 1-N-(glycyl-L-α,γ-diaminobutyryl) sisomicin and 1-N-(L-α-γ-diaminobutyryl-glycyl) sisomicin.

9. A compound of claim 8, said compound being 1-N-(L-diglycyl) sisomicin.

10. A compound of claim 8, said compound being 1-N-(L-leucyl-glycyl) sisomicin.

11. A compound of claim 8, said compound being 1-N-(glycyl-L-leucyl) sisomicin.

12. A compound of claim 8, said compound being 1-N-(glycyl-L-seryl) sisomicin.

13. A compound of claim 8, said compound being 1-N-(L-seryl-glycyl) sisomicin.

14. A compound of claim 8, said compound being 1-N-(glycyl-L-α,ν-diaminobutyryl) sisomicin.

15. A compound of claim 8, said compound being 1-N-(L-α,γ-diaminobutyryl-glycyl) sisomicin.

16. A 1-N-(diglycyl) derivative of a compound of claim 4, said derivative being 1-N-(diglycyl) gentamicin B.

17. A compound of claim 7, said compound being a 1-N-tripeptidyl derivative of sisomicin.

18. A compound of claim 17, said compound being 1-N-(triglycyl) sisomicin.

19. A method of eliciting an antibacterial response in a warm blooded animal having a bacterial infection caused by a susceptible bacteria which comprises administering to said animal a compound selected from the group consisting of 1-N-peptidyl derivatives of 4,6-di-0-(aminoglycosyl)-1,3-diaminocyclitol antibacterial agents including the non-toxic pharmaceutically acceptable acid addition salts thereof wherein said peptidyl moiety is derived from the group consisting of

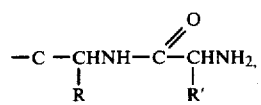

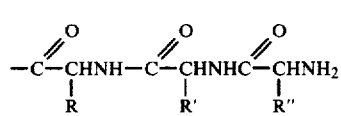

wherein R, R' and R" may be the same or different, are attached to carbon atoms which are in the L or D configuration, said R, R' and R" being members selected from the group consisting of hydrogen; $C_1$-$C_6$ alkyl including branched chain alkyl; HO—$(CH_2)_{\overline{n}}$; HO—$(CH_3)$CH—; HO—$(CH_3)_2$C—; $NH_2$—$(CH_2)_{\overline{n}}$; $NH_2$—$CH_2$—CH(OH)—$(CH_2)_{\overline{n}}$;

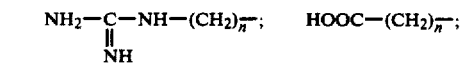

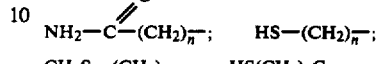

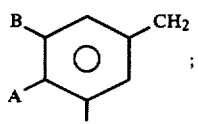

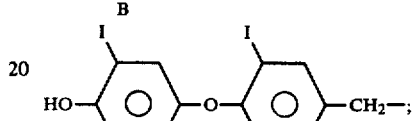

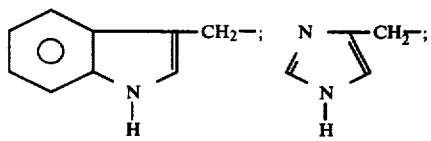

wherein A is a member of the group consisting of hydrogen and hydroxy; B is a member selected from the group consisting of hydrogen, bromo and iodo; D is a member selected from the group consisting of hydrogen and iodo; n is an integer from 1-5 and wherein R, R' and R" may be linked to the respective α-nitrogen to form a cyclic moiety selected from the group consisting of:

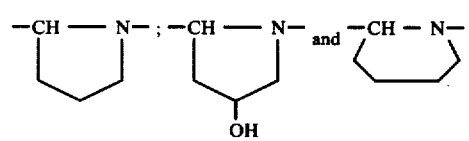

and wherein the compound is administered at from about 7.5 to about 15 mg/kg/day.

20. A method according to claim 19 which comprises administering a compound of said claim wherein the acyl moiety has the formula

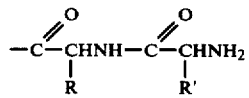

and wherein R and $R_1$ are as defined in said claim 19.

21. A method according to claim 19 which comprises administering a compound of said claim wherein the acyl moiety has the formula

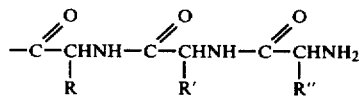

and wherein R, R' and R" are as defined in said claim 19.

22. A method of eliciting an antibacterial response in a warm blooded animal having a bacterial infection caused by a susceptible bacterial which comprises administering to said animal from about 7.5 to about 15 mg/kg/day of a compound of claim 4.

23. A method of eliciting an antibacterial response in a warm blooded animal having a bacterial infection caused by a susceptible bacteria which comprises administering to said animal from about 7.5 to about 15 mg/kg/day of a compound of claim 5.

24. A method of eliciting an antibacterial response in a warm blooded animal having a bacterial infection caused by a susceptible bacteria which comprises administering to said animal from about 7.5 to about 15 mg/kg/day of a compound of claim 6.

25. A method of eliciting an antibacterial response in a warm blooded animal having a bacterial infection caused by a susceptible bacteria which comprises administering to said animal from about 7.5 to about 15 mg/kg/day of a compound of claim 7.

26. A method of eliciting an antibacterial response in a warm blooded animal having a bacterial infection caused by a susceptible bacteria which comprises administering to said animal from about 7.5 to about 15 mg/kg/day of a compound of claim 8.

27. A method according to claim 22 wherein 1-N-(diglycyl) sisomicin is administered.

28. A method according to claim 22 wherein 1-N-(diglycyl) gentamicin B is administered.

29. A method according to claim 25 wherein 1-N-(triglycyl) sisomicin is administered.

* * * * *